(12) United States Patent
Marcos Celestino et al.

(10) Patent No.: US 10,383,721 B2
(45) Date of Patent: Aug. 20, 2019

(54) PHOTOCHEMICALLY INDUCED ENGAGEMENT OF INTRAOCULAR IMPLANTS

(71) Applicants: CONSEJO SUPERIOR DE INVESTIGACIONES CIENTÍFICAS, Madrid (ES); THE GENERAL HOSPITAL CORPORATION, Boston, MA (US)

(72) Inventors: Susana Marcos Celestino, Madrid (ES); Carlos Dorronsoro Díaz, Madrid (ES); Nicolás Alejandre Alba, Madrid (ES); Andrés De La Hoz Durán, Madrid (ES); Irene Emily Kochevar, Boston, MA (US)

(73) Assignees: CONSEJO SUPERIOR DE INVESTIGACIONES CIENTÍFICAS, Madrid (ES); THE GENERAL HOSPITAL CORPORATION, Boston, MA (US)

( * ) Notice: Subject to any disclaimer, the term of this patent is extended or adjusted under 35 U.S.C. 154(b) by 5 days.

(21) Appl. No.: 15/556,861

(22) PCT Filed: Mar. 10, 2016

(86) PCT No.: PCT/EP2016/055191
§ 371 (c)(1),
(2) Date: Sep. 8, 2017

(87) PCT Pub. No.: WO2016/142490
PCT Pub. Date: Sep. 15, 2016

(65) Prior Publication Data
US 2018/0271646 A1     Sep. 27, 2018

(30) Foreign Application Priority Data
Mar. 10, 2015   (EP) .................................. 15382106

(51) Int. Cl.
*A61F 2/16*     (2006.01)
*A61F 9/007*    (2006.01)
*A61F 9/008*    (2006.01)

(52) U.S. Cl.
CPC .......... *A61F 2/1624* (2013.01); *A61F 9/0079* (2013.01); *A61F 9/008* (2013.01);
(Continued)

(58) Field of Classification Search
CPC .......... A61F 2002/16965; A61F 2/1624; A61F 2/1694; A61F 2002/1681;
(Continued)

(56) References Cited

U.S. PATENT DOCUMENTS 5,002,571 A * 3/1991 O'Donnell, Jr. .......... A61F 2/16
                                                        623/6.11
5,133,748 A * 7/1992 Feaster ............ A61B 17/00491
                                                        623/6.12
(Continued)

FOREIGN PATENT DOCUMENTS

GB        2105866 A    3/1983
WO      9113597 A1    9/1991
(Continued)

OTHER PUBLICATIONS

International Search Report dated May 4, 2016 re: Application No. PCT/EP2016/055191; pp. 1-5; citing: WO 2011/031557 A1, WO 91/13597 A1, GB 2 105 866 A, US 6 410 044 B1, WO 2014/152017 A1, WO 98/25180 A1 and WO 2012/122281 A2.
(Continued)

*Primary Examiner* — David H Willse
*Assistant Examiner* — Javier G Blanco
(74) *Attorney, Agent, or Firm* — Cantor Colburn LLP

(57) ABSTRACT

An ocular implant and a method for implanting such an ocular implant inside an eye includes an optical portion and
(Continued)

at least two polymer haptics for fixation of the ocular implant to tissue inside an eye. At least one portion of the haptics contains a photoinitiating agent delivery component. A kit for implanting an ocular implant in an eye includes an ocular implant at least two polymer haptics; and additionally a photoinitiating agent for at least partially impregnating a first portion of the ocular element or a second portion of tissue in the eye; and, a light source for providing light of a wavelength adapted to excite the photoinitiating agent.

7 Claims, 4 Drawing Sheets

(52) U.S. Cl.
CPC ....... *A61F 9/00821* (2013.01); *A61F 9/00834* (2013.01); *A61F 2002/1681* (2013.01); *A61F 2220/0008* (2013.01); *A61F 2250/0067* (2013.01)

(58) Field of Classification Search
CPC .... A61F 2002/1682; A61F 2002/16901; A61F 9/00821; A61F 2220/0008; A61F 9/00834
See application file for complete search history.

(56) References Cited

U.S. PATENT DOCUMENTS

| | | | |
|---|---|---|---|
| 5,607,472 A * | 3/1997 | Thompson | A61F 2/1613 623/6.13 |
| 6,106,550 A | 8/2000 | Magovern et al. | |
| 6,193,750 B1 | 2/2001 | Cumming | |
| 6,410,044 B1 | 6/2002 | Chudzik et al. | |
| 6,702,853 B1 * | 3/2004 | Peyman | A61F 2/1602 623/6.12 |
| 7,150,760 B2 | 12/2006 | Zhang | |
| 7,331,350 B2 * | 2/2008 | Kochevar | A61F 9/0079 128/898 |
| 2003/0204254 A1 | 10/2003 | Peng et al. | |
| 2005/0113911 A1 * | 5/2005 | Peyman | A61F 2/1613 623/6.11 |
| 2008/0140192 A1 | 6/2008 | Humayun et al. | |
| 2010/0063588 A1 * | 3/2010 | Park | A61F 2/1635 623/6.23 |
| 2011/0029074 A1 * | 2/2011 | Reisin | A61F 2/1613 623/6.39 |
| 2011/0054601 A1 * | 3/2011 | Kadziauskas | A61F 2/1635 623/6.39 |
| 2011/0307058 A1 | 12/2011 | Beer | |
| 2012/0035527 A1 * | 2/2012 | Tearney | A61L 27/3604 604/20 |
| 2012/0310343 A1 * | 12/2012 | Van Noy | A61F 2/1635 623/6.39 |
| 2013/0190737 A1 * | 7/2013 | Muller | A61F 9/0079 606/6 |
| 2015/0265398 A1 * | 9/2015 | Hartkens | A61F 9/00821 623/6.43 |

FOREIGN PATENT DOCUMENTS

| | | |
|---|---|---|
| WO | 9635398 A1 | 11/1996 |
| WO | 9825180 A1 | 6/1998 |
| WO | WO 2011/031557 A1 | 3/2011 |
| WO | 2012122281 A1 | 9/2012 |
| WO | 2014152017 A1 | 9/2014 |

OTHER PUBLICATIONS

Written Opinion dated May 4, 2016 re: Application No. PCT/EP2016/055191; pp. 1-7; citing: WO 2011/031557 A1.

* cited by examiner

PHOTOCHEMICALLY INDUCED ENGAGEMENT OF INTRAOCULAR IMPLANTS

TECHNICAL FIELD

The present disclosure relates to ophthalmic implants and related methods, and more particularly to intraocular lenses, including those aiming at restoring accommodation.

BACKGROUND

The optical system of the eye is composed by refractive elements (cornea and lens) and aqueous and vitreous humors. The crystalline lens of the eye is the second lens in the eye, behind the cornea and the iris. In the emmetropic eye the optical power of the cornea and crystalline lens are such that the optical image is projected sharply on the retina. In the young eye the crystalline lens can alter its shape to accommodate near and far objects. This capability is lost with age (a condition called presbyopia). Also, the normal lens is transparent. Also with aging, the crystalline lens opacifies (a condition called cataract).

The crystalline lens can be replaced by an artificial intraocular lens (IOL) to correct for refractive errors in non-emmetropic eyes, and more commonly, to correct for cataract. Recently, intraocular lenses that aim at restoring the accommodation capability of the eye (i.e. correcting presbyopia) have been proposed. These accommodating IOLs (A-IOLs) are intended to use of the accommodative forces transmitted from the ciliary muscle to the lens by the zonulae and the lens capsule, to shift axially or laterally one of more elements, or reshape the geometry of the lens.

Most intraocular lens designs have a central optical zone and two or more haptics to hold the lens in place inside the capsular bag, and to guarantee IOL stability and centration. While intracapsular cataract surgery has proved safe and in most cases uneventful, post-operative problems may arise associated to capsular fibrosis that results from anterior capsule epithelial cells proliferation and migration. Capsular fibrosis may result in posterior capsule opacification (and the need of a secondary surgery) and capsular bag contraction and IOL misalignment.

An alternative IOL design aimed at preventing the effects of capsular fibrosis and opacification is that of the so-called "bag in the lens". In this technique the peripheral groove of the lens allows holding the anterior and posterior capsulorhexis (surgically performed window edges) of the capsular bag.

Haptic design is of particular relevance in A-IOLs, as they require the transmission of forces from the accommodative implant into the lens. The mechanism of operation of several accommodating IOL designs requires the capsular bag to operate similarly to that in the intact eye, although it is likely that fibrosis following cataract surgery will compromise these mechanisms.

An identified problem of several accommodating IOLs is the lack of a strong connection with the capsular bag that is needed for adequate transfer of forces from the ciliary muscle to the action mechanism of the lens; this is the case of the two optic accommodative lens system disclosed in patent document U.S. Pat. No. 7,150,760.

Some A-IOLs require that the connection between the haptics and the periphery of the capsular bag is produced by natural fibrosis occurring during the weeks following implantation. However, this uncontrolled process may result in a limitation of the shifting or reshaping mechanism of the A-IOL.

Some patent documents disclose haptic devices that depend on the fibrosis process, such as U.S. Pat. No. 6,193,750. US-2011/0307058 proposes the zonular capture haptic, which favors the fusion of the capsular bag to the haptics, assisted by the natural process of fibrosis. This approach requires two surgical acts separated by days, in which the haptic platform and the A-IOL are implanted, respectively. Relying on the natural fibrosis for the engaging the A-IOL to the capsular bag has several drawbacks, including the duration of the process, uncertainty in the A-IOL alignment, and the final outcome of the engagement. Nevertheless, engagement of the haptic to the capsule is critical in several A-IOL designs.

Patent document US-2003/0204254 proposes mechanical engagement of the lens haptic (or lens periphery) to the edge of the capsulorhexis using mechanical blocking arms or clasps. A drawback of such a mechanical attachment to the capsule is the potential tearing or rupture of the capsule.

An alternative to the use of mechanical capsule-IOL engagement system is the use of bio-adhesives. Bio-adhesive materials are increasingly used in medicine for tissue repair in surgery, drug delivery, or attachment of prosthetic devices. For example, patent document US-2008/0140192 discloses the use of a reversible thermo-responsive adhesive substance for attaching microelectronic retinal implants to the retinal tissue. This particular polymer has the property of becoming adhesive to cells above a critical temperature, 32°, in aqueous environments.

The use of bio-adhesive polymers has been recognized as advantageous in applications where an intraocular lens requires a firm attachment to the capsular bag to transmit the forces of the accommodative plant into an A-IOL mechanism. Patent document WO-96/35398 suggests thermal adhesion of the peripheral part of an IOL (coated with an adhesive material) to the anterior capsulorhexis, by increasing temperature with a laser to produce thermal welding of the IOL material and the capsular bag tissue.

Patent document US-2011/0029074 proposes the use of a thermo-reversible material for applications in intraocular surgery, including A-IOL implantation and stunt implantation in glaucoma. In this document they also recognize the need for effectively translating the ocular forces of the natural accommodative mechanism to maximize the accommodation amplitude of A-IOLs, and propose the use of polymeric systems that may modify their adhesive properties in response to changes of the physical and chemical characteristics of the physiological medium. In particular, they propose the use of a thermo-reversible adhesive polymer coating the surface of certain areas of a haptic structure (and possibly the surface of the IOL) to favor the adhesion of the system to the capsular bag. The thermo-adhesive polymer would exhibit adhesive properties at body temperature. Irrigation with cold or room temperature solution during the surgical procedure, or possibly for explanation could produce detachment of the IOL/haptic from the capsular bag. Although pNIPAM polymer is described as a biocompatible non-toxic substance to neural tissue or cultured cells, its intraocular non-toxicity has never been proven. The non-polymerized form NIPAM has been proven toxic to neural tissue. On the other hand, the dynamical properties of the pNIPAM adhesive when deposited as a thin layer across the capsulorhexis have not been proven and it is not clear whether it may remain for sufficient time to produce a thermo-adhesive response.

The use of photo-chemically induced bonding processes is also known. The use of localized light delivery is particularly well suited intraocularly, as done in several procedures, including retinal photocoagulation or laser trabeculoplasty in glaucoma. The use of localized irradiation in internal body organs is generally performed by the use of catheters for visualization, sensing or treatment. For example, as described in patent document U.S. Pat. No. 6,106,550, light can be conducted through a fiber and emitted from its end into the surroundings for purposes of, among others, illumination or for cutting tissue with a laser beam.

Also, a photo-activated process is used in corneal collagen cross-linking for the treatment of keratoconus by tissue stiffening. In this procedure, formation of inter- and intra-fibrillar bonding is produced by the instillation of a photosensitizer (typically a riboflavin-containing solution) and irradiation with UVA light. Corneal collagen photo-cross-linking has also been demonstrated with other photosensitizers, such as Rose Bengal, and irradiation with green light. One of the advantages of the use of Rose Bengal is that it is an FDA-approved compound of widespread use in ophthalmology, for example in dry eye staining tests. In addition, intracapsular use of Rose Bengal has proved non-toxic in rabbit eye models. The use of photosensitizers and photo-activation is described in U.S. Pat. No. 7,331,350 to produce heat-free bonding of damaged tissue for repair, therefore replacing sutures of staples. These photochemical tissue-bonding methods include the application of a photosensitizer to tissue (i.e. the cornea) followed by irradiation with electromagnetic energy to produce a tissue-tissue seal, in the absence of an exogeneously supplied source of cross-linkable structure. It is thought that in photochemical bonding that activation of the photoinitiator by light absorption produces structural changes in the amino acids of the proteins of the tissue and formation of covalent bonds between collagen molecules on opposing surfaces of the two tissues in contact.

Therefore, there is a need for an accommodating intraocular lens that can be securely fixed to the capsular eye by means of a non-toxic process and, at the same time, providing sufficient resistance to rupture.

SUMMARY

In the present disclosure, the use of a photochemically induced bonding is proposed in situations requiring intraocular engagement of a polymer implant to ocular tissue, such as the implantation of an intraocular lens in the eye, such as in cataract surgery, or in spresbyopia or refractive surgery with intraocular lens implants.

The present disclosure is mainly based on the fact that intraocular tissue bonds tightly to a polymer material, such as pHEMA, upon the application of a photosensitizer and irradiation with light. In the present disclosure the attachment to tissue of an implant having at least a polymeric portion that will come into contact with the tissue is performed by applying a photosensitizer in a portion of the tissue and/or a portion of the implant and then by irradiating with light, in the absence of any exogenously supplied source of cross-linkable substrate, tissue adhesive or glue.

The tissue and implant to be bonded are placed in close contact, during which time light irradiation is applied to produce photochemical engagement of the tissue and the implant. The inventors have proven that tight bonding occurs even in the absence of collagen or proteins in the material.

The photochemical bonding between tissue and a polymer material according to the present disclosure is particularly useful and specially advantageous with accommodating IOLs, where it is necessary that the forces from the ciliary body are directly transmitted to the mechanism of the accommodating IOL (AIOL) to alter the shape of a deformable element, or to change the axial position of one or more elements of the lens. This direct transmission of the forces of the ciliary body and the implant IOL is achieved by means of the resulting photobonded portions.

A first aspect of the disclosure relates to an ocular implant, which comprises:
an optical portion; and,
at least two polymer haptics for fixation of the ocular implant to tissue inside an eye;
wherein at least one portion of the haptics contains a photoinitiating agent delivery means or means for delivering a photoinitiating agent.

That is, the ocular implant comprises two or more polymer haptics, and at least one portion of each haptic—which will come into contact with the eye tissue—contains a photoinitiating agent (it is made of or coated with, a material containing a photoinitiating agent), so that that portion of the haptics is, per se, capable of providing the photoinitiating agent. Or the at least one portion of the haptics which is appropriate for contacting the eye tissue is provided with means for delivering the photoinitiating agent, which may be kept in some sort of deposit or enclosure embedded within the haptics, or in a container or source external to the haptics; such delivery means can comprise multiple microfluidic channels or a membrane, through which the photoinitiating agent can flow and be delivered at an outer surface of the haptics.

In particular, the present disclosure describes a haptic structure which is photochemically-bonded to the capsular bag to engage the mechanical forces of the accommodative mechanism in an A-IOL to restore accommodation.

By ocular implant it is meant an artificial functional implantable device that restores a function that is compromised or lost in the eye. Preferably, the ocular implant is an intraocular lens, and more preferably an accommodating IOL.

The at least two haptics of the implantable device are polymer haptics, that is, they are made of a polymer material, or they are coated with a polymer material, or they have a portion made of a polymer material.

By polymer material it is understood any suitable biocompatible polymer, and more preferably HEMA derivatives such as pHEMA, pHEMA-MMA, pHEMA-GMA, etc.

By photoinitiating agent or photoinitiator is understood is any chemical compound that generates free radicals or other reactive chemical species from components in the tissue when exposed to light.

The optical portion of the ocular implant is preferably able to change its optical power in response to a force applied thereto.

In a preferred embodiment, the photoinitiating agent delivery means comprises an outer surface of the haptics being coated with the photoinitiating agent or such outer surface comprising an outer layer of the haptics where the photoinitiating agent is embedded.

In this preferred embodiment, the ocular implant may be introduced in an eye where the polymer haptics are deployed and spread out inside the eye, causing the haptics, which outer surfaces are impregnated with the photoinitiating agent or have the photoinitiating agent embedded in the outer surface, to contact with the capsular bag. By irradiating that contact portion with an external or internal light source the photochemical bond in the contact portion between the polymer haptics and the eye tissue is produced.

In another preferred embodiment the photoinitiating agent delivery means comprises multiple microfluidic channels through which the photoinitiating agent can flow, such microfluidic channels being arranged such that the photoinitiating agent is delivered in an outer surface of the haptics. The photoinitiating agent can be contained in a reservoir provided in the ocular implant or it can be injected from an external reservoir through the microfluidic channels.

In a preferred embodiment the ocular implant further comprises means for making the implant to be in a stretched state; in such a state the haptics better contact the capsular bag.

This means for making the implant to be in a stretched state may comprise at least one tension ring, such as a capsular tension ring.

In another preferred embodiment, the means for making the implant to be in a stretched state may comprise at least one balloon.

The means for making the implant to be in a stretched state are preferably located with respect to the haptics such that it transmits a centrifugal force to the haptics. For instance, the haptics may comprise curved plates, and the tension ring or the balloon are located in an inner surface of the plates, such that when the tension ring is tensioned or the balloon inflated the haptics are pushed outwards in a radial direction.

As outlined above, the ocular implant of the present disclosure may further comprise light guiding elements; these light guide elements may be embedded in the haptics.

In other embodiments, these light guiding elements can be embedded or be part of the means for making the implant to be in a stretched state. For instance, the light guiding elements can be embedded in the outer perimeter of the tension ring or the balloon.

The means for making the implant to be in a stretched state can be removable or deactivatable, such that once the light has been irradiated and the photobonding has taken place the means that stretch the ocular implant can be removed or deactivated.

Since the ocular implant is to be used in a human body, it should be safely preserved from being infected or contaminated till the implantation. Therefore, the ocular implant of the present disclosure may be additionally coated or embedded in a preserving composition in order to guarantee the correct storing and optimal state for implantation. The preserving solution can protect the ocular implant from external infection or contamination and it can function not to cause endophthalmitis during implantation into the human body. The composition for preserving an artificial intraocular lens of the disclosure may comprise a wetting agent, an antimicrobial agent, a stabilizer, an isotonic agent, a solubilizing aid, a viscosity adjuster, an antioxidant or a buffering solution. Thus, in a preferred embodiment, the ocular implant as described in the present disclosure is coated or embedded in a preserving composition, more preferably this preserving composition comprises a wetting agent, an antimicrobial agent, a stabilizer, an isotonic agent, a solubilizing aid, a viscosity adjuster, an antioxidant and/or a buffering solution.

A second aspect of the disclosure relates to a kit for implanting an ocular implant in an eye, the kit comprises:
the ocular implant to be implanted comprising at least two polymer haptics;
a photoinitiating agent for at least partially impregnating a first portion of the ocular implant and/or a second portion of tissue in the eye; and,
a light source for providing light of a wavelength adapted to excite the photoinitiating agent.

The ocular implant in the kit is preferably in accordance with the ocular implant defined hereinbefore.

In some embodiments the kit preferably further comprises:
means for making the implant to be in a stretched state; and
means for delivering the light provided by the light source into the eye.

These further elements facilitate the implantation and photobonding procedure, by stretching the lens radially (particularly useful in accommodating IOL implantation), by achieving the contact of the haptics with the capsular bag equator, and by allowing proximal delivery of the light to the area to be photobonded.

The means for making the implant to be in a stretched state preferably comprise at least one tension ring or at least one balloon, which may be part of the ocular implant. The means are preferably removable, so that they can be removed once the ocular implant has been implanted in the eye. The means for delivering the light provided by the light source into the eye comprises light guiding elements, which may be preferably embedded in the at least one tension ring or the at least one balloon.

As indicated before, the photoinitiator or photoinitiating agent is any chemical compound that absorbs the energy of light when exposed to it, the light preferably being ultraviolet, visible or near infrared radiation. Examples of photoinitiators include various light-sensitive dyes and biological molecules such as, for example, Rose Bengal, riboflavin, eosin Y, methylene blue, porphyrins, thioxanthenes, bacteriochloropylls, phenothiazines, cyanines, quinones and photosensitive derivatives thereof.

In a preferred embodiment the photoinitiating agent is a solution containing Rose Bengal, and it is photoactivated with a light source providing light having green wavelengths. In another embodiment the photoinitiating agent is a solution containing Riboflavin, photoactivated with a light source providing light having UV wavelengths. In other embodiments the photoinitiating agent is another photoactivable component, activated at another particular wavelength of light.

A further aspect of the disclosure refers to a method for implanting an ocular implant inside an eye, the method comprising the following steps:
i) introducing the ocular implant inside the eye, wherein a first portion of the ocular implant and/or a second portion of tissue in the eye contains a photoinitiating agent in their surface; and
ii) irradiating said first portion and/or said second portion with light when there is contact between the first portion of the ocular implant and the eye tissue or between the ocular implant and the second portion of the eye tissue;
such that the ocular implant is photochemically bonded to the eye.

Another aspect of the disclosure refers to a method for implanting an ocular implant inside an eye, the method comprising the following steps:
i) impregnating a first portion of the ocular implant or a second portion of the eye tissue with a photoinitiating agent or both;
ii) introducing the ocular implant inside the eye; and, iii) irradiating said first portion and/or said second portion with light when there is contact between the first portion of the ocular implant and the eye tissue or between the ocular implant and the second portion of the eye tissue;

such that the ocular implant is photochemically bonded to the eye.

In either method, in order to make sure that there is firm contact between the first portion of the ocular implant and the eye tissue, the method preferably further comprises making the ocular implant to be in a stretched state prior to irradiating with light.

In either method, light is irradiated preferably for a duration less than 600 s, and more preferably for less than 180 s.

The step of irradiating with light is preferably carried out at irradiance below 0.65 W/cm$^2$.

The ocular implant used in either method is preferably in accordance with the ocular implant defined hereinbefore.

In a further aspect of the disclosure an ocular implant is defined, which comprises:
an optical portion; and,
at least two polymer haptics;
the ocular implant further comprising:
at least one fixing portion for affixing the ocular implant to tissue inside an eye, the fixing portion being generated by photochemically inducing a bond on an overlapping area between the haptics and the eye tissue.

The different aspects and embodiments of the disclosure defined in the foregoing can be combined with one another, as long as they are compatible with each other.

Additional advantages and features of the disclosure will become apparent from the detailed description that follows and will be particularly pointed out in the appended claims.

BRIEF DESCRIPTION OF THE DRAWINGS

To complete the description and in order to provide for a better understanding of the disclosure, a set of drawings is provided. Said drawings form an integral part of the description and illustrate an embodiment of the disclosure, which should not be interpreted as restricting the scope of the disclosure, but just as an example of how the disclosure can be carried out. The drawings comprise the following figures.

DETAILED DESCRIPTION OF THE DRAWINGS

Figure 1:
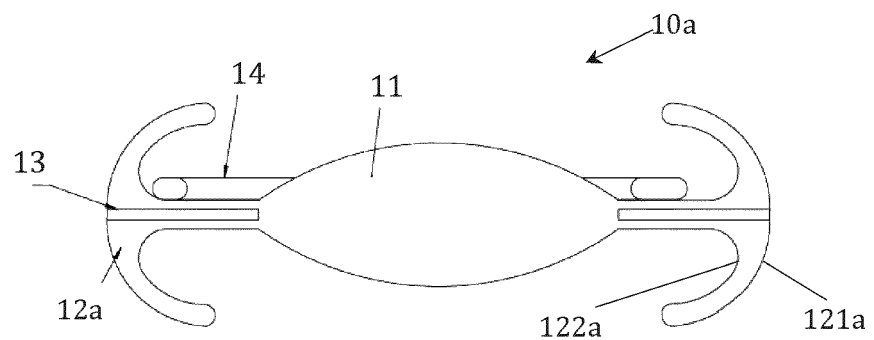
FIG. 1 shows a cross-section view of an intraocular lens according to a first possible embodiment of the disclosure.
Figure 2:
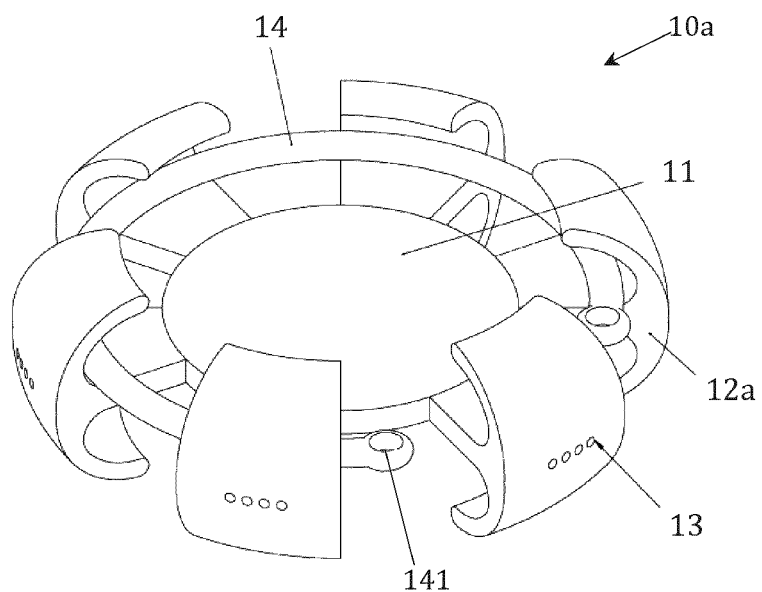
FIG. 2 shows a perspective view of the intraocular lens of FIG. 1.

FIGS. 1 and 2 show an ocular implant 10a according to a first possible embodiment of the disclosure, which is designed to engage the capsular bag using photobonding.

The ocular implant 10a comprises a deformable lens with a central optical portion 11 and a number of haptics 12a—six in this preferred embodiment—, which are uniformly distributed along an equatorial region of the central optical portion 11 of the lens. These haptics 12a extend radially from the edge of the central optical portion 11, and comprise free ends in the shape of transverse curved plates in order to facilitate the transfer of the ciliary muscle forces to the lens.

In this first preferred embodiment, the haptics 12a contain a number of small microfluidic channels 13 through which a photosensitizer can flow from the lens or haptics towards an external convex surface 121a of the haptics 12a and a portion of the capsular bag that is to be in contact with the lens 10a, in order to stain them.

The haptics 12a are made of a pHEMA-based polymer material and the photosensitizer applied through microfluidic channels 13 is Rose Bengal.

The ocular implant further comprises a removable capsular tension ring 14. This tension ring 14 is a cylindrical flexible body having a manipulation hole 141 at each of its ends. The tension ring 14 is arranged in the internal concave portion 122a of some of the haptics 12a or all of them, and is used to stretch the ocular implant 10a so as to apply pressure to the haptics. This maximizes contact between the haptics 12a and the capsular bag.

Figure 3:
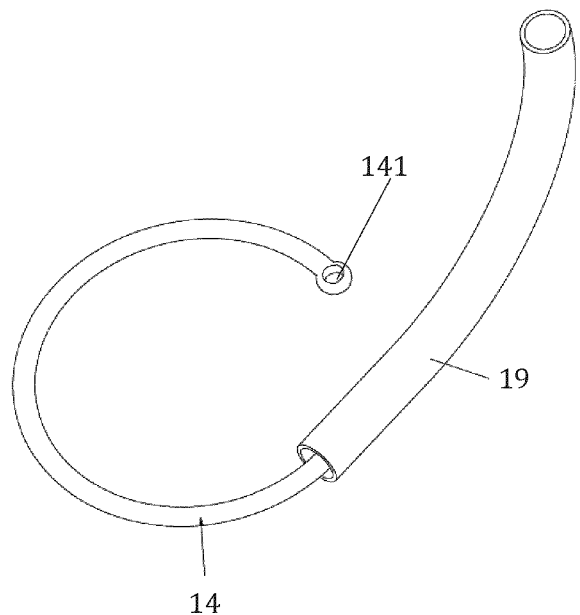
FIG. 3 shows an embodiment of the removable capsular tension ring.

Additionally, and as shown in detail in FIG. 3, the removable capsular tension ring 14 is attached to a probe 19 so that light can be transmitted through the probe and into the tension ring 14 so that it is capable of guiding light along the its entire length, and release the light required for photobonding in specific sites throughout its outer perimeter, including irradiating areas of the haptics 12a in contact with the capsular bag. In this preferred embodiment the light used has a green wavelength.

In the case shown in the drawings the capsular tension ring 14 is removable, but it is also possible that the tension ring is not removable but it can be deactivated once the light has been irradiated and the photobonding has been achieved.

The capsular tension ring shown in FIGS. 1 and 2 has two manipulation holes 141 at its ends. It is also possible that it has one or more manipulation hooks—not shown in the drawings—which are also valid for manipulating the ring.

Figure 4:
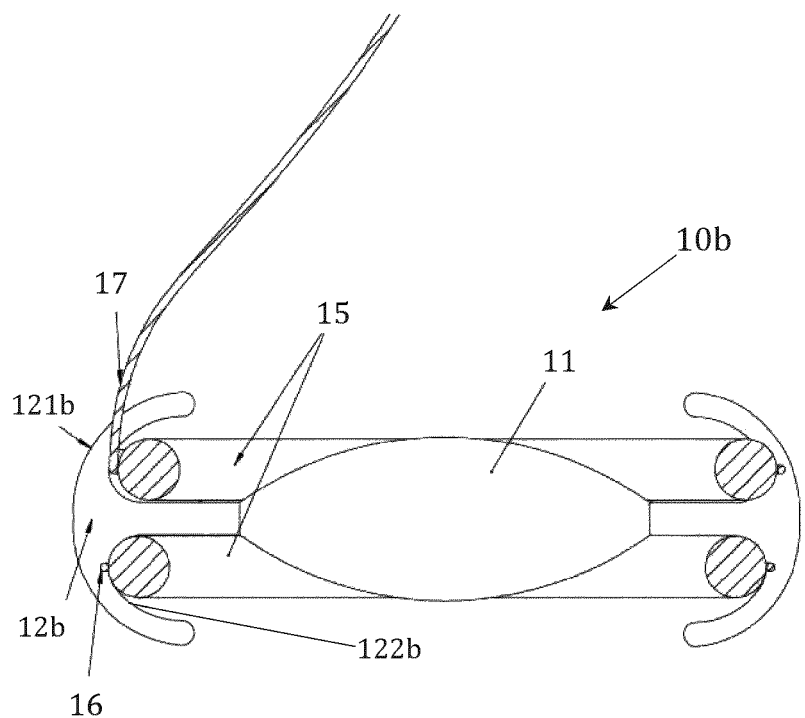
FIG. 4 shows a section view of an intraocular lens according to a second possible embodiment of the disclosure.
Figure 5:
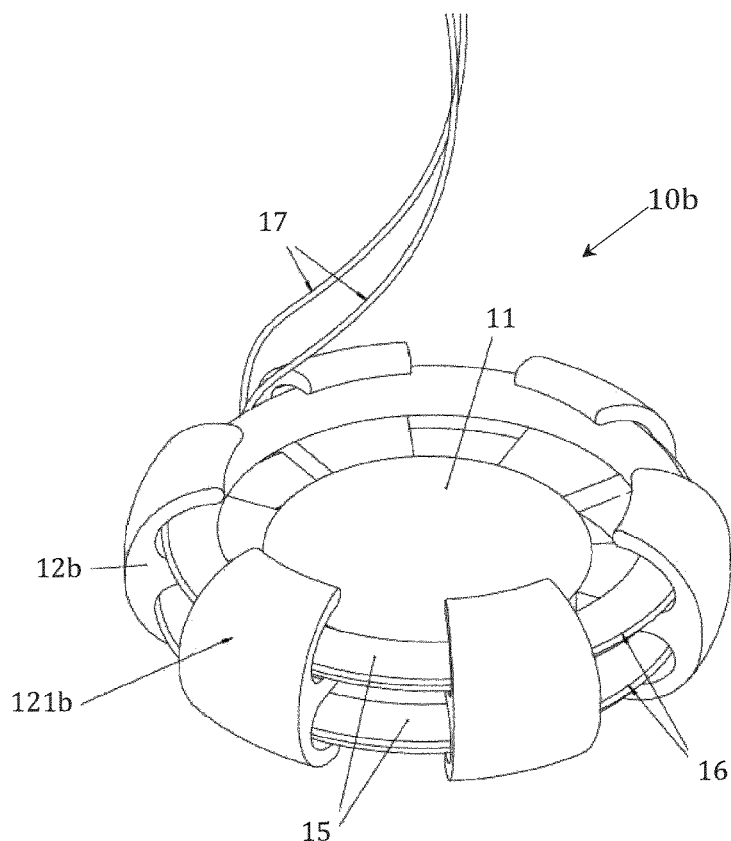
FIG. 5 shows a perspective view of the intraocular lens of FIG. 3.

FIGS. 4 and 5 show an ocular implant 10b according to second possible embodiment of the disclosure, which is designed to engage the capsular bag using photobonding.

The ocular implant 10b comprises a deformable lens with a central optical portion 11 with a number of haptics 12b—six in this preferred embodiment—, which are uniformly distributed along an equatorial region of the central optical portion 11 of the lens. The haptics 12b in this embodiment also extend radially from the edge of the central optical portion 11, and comprise free ends in the shape of transverse curved plates in order to facilitate the transfer of the ciliary muscle forces to the lens.

In this case, an external convex surface 121b of the haptics 12b is coated with a photosensitizer, which is shown as shaded in FIG. 4.

The haptics 12b are made of a poly-hydroxyethylmethacrylate (pHEMA)-based polymer material and the photosensitizer coating the external surface 121b of the haptics is Rose Bengal.

The ocular implant further comprises one or two removable torus-shaped inflatable balloons 15, similar to a balloon catheter, with embedded fiber optics 16 along the outer edge of the balloon 15. Although not shown in the drawings, it is possible that the balloon is transparent and that the fiber optics is embedded inside the balloon instead of being embedded or extending along the perimeter of the balloon.

The one or two balloons 15 are arranged in the internal concave portion 122b of the haptics 12b, and are used both to stretch the implantable device 10b so as to apply pressure to the haptics and to provide contact and light distribution as explained below.

The inflation of the balloon or balloons 15 is controlled externally by means of a cannula 17. Upon inflation, the balloon 15 stretches the implantable device 10b and presses its haptics 12b against the capsular bag, to provide close contact between the haptics 12b and the capsular bag needed for photobonding.

The embedded fiber optics 16 guides light injected by the cannula 17, and releases light throughout its perimeter, thereby irradiating areas of the haptics in contact with the capsular bag.

In a preferred embodiment of this ocular implant 10b, the balloon 15 contains micro-pores (not shown in the figures) that release air or oxygen during inflation, so as to facilitate the oxygen-requiring photochemical reaction.

In either case, the balloons 15 are de-inflated and removed after photobonding. The light guided into the fiber optics has a green wavelength.

The following example illustrates an experimental procedure followed for implanting a body made of a polymer material to the capsular bag by photobonding.

Capsular bags were obtained from freshly enucleated New Zealand albino rabbit eyes, less than 12 hours post-mortem. A circular section of the anterior capsule of the largest possible diameter (7-10 mm) was removed from the eye under an opthalmological surgical microscope, using capsular scissors and immersed in a buffered saline solution BSS. Strips of capsule (5×7-10 mm) were cut and reserved for testing in the buffered saline solution.

The polymer material used was a copolymer of pHEMA and GMA, provided by Vista Optics Ltd under the commercial name of VistaflexAdvantage +49. Samples of the copolymer material were cut, using a precision optics diamond-fiber cutter into 5×10 mm rectangular strips, of 1 mm thickness. The water content of the material is 49% in a hydration state. Each piece was dehydrated and then rehydrated in a Rose Bengal 0.1% solution.

The Rose Bengal 0.1% solution was prepared dissolving 0.01 g of commercial Rose Bengal sodium salt (provided by Sigma Aldrich) into 10 ml of a phosphate buffered solution (PBS).

The custom-developed light delivery system used in this experiment consisted of a pumped all-solid-state green laser source (provided by CNI Tech, Co. Ltd, China), with a central wavelength of 532 nm and an output power of 1300 mW and 1100 mW at the end of the fiber. The fiber tip is placed in the focal point of a 150-mm focal length lens. The sample holder is placed one focal length after the collimating lens. The light delivery system has neutral density filters which allow changing the laser power density at the sample plane between 0.65 and 0.25 $W/cm^2$.

Capsular bag strips were stained in Rose Bengal by immersion in the Rose Bengal solution for 2 minutes. The capsular bag strips were placed and deployed on top of the pHEMA-GMA strips, so that about half of the capsular bag strip and polymer strip overlapped, and they were placed in the sample holder of the light delivery system. Exposure times ranged between 30 and 180 s, and laser irradiances between 0.25 and 0.65 $W/cm^2$.

The strength of the bonding was tested using uniaxial extensiometry. For this testing the capsular bag end and the pHEMA end were clamped in a custom-developed extensiometry system, provided with piezo-motors and load sensors. The different loads were achieved by displacing each arm in 0.1 mm-steps, and the load producing a breakage in the capsule-pHEMA bonding was measured.

Figure 6:
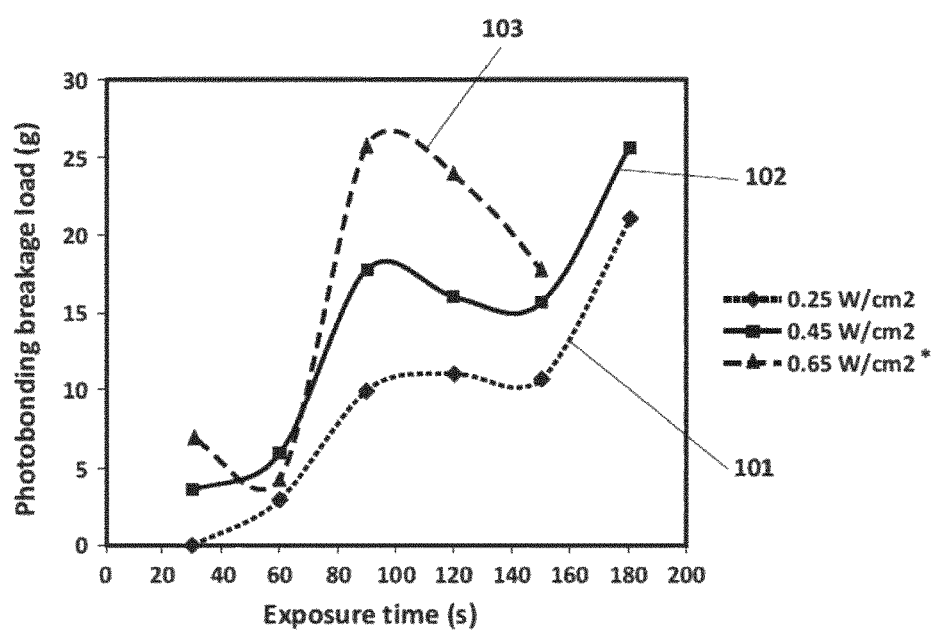
FIG. 6 is a diagram showing the influence of the radiation exposure times and irradiance on the strength of the bond between the ocular implant and the capsular bag.

FIG. 6 shows the loads that produced breakage of the capsule-pHEMA bonding as function of irradiation time, for three different laser irradiances: 0.25 $W/cm^2$ (curve 101), 0.45 $W/cm^2$ (curve 102) and 0.65 $W/cm^2$ (curve 103).

As can be seen, increasing exposure time and laser irradiance levels increases the breakage point of the bond created. Exposure times higher than 90 s at all tested laser irradiance levels produced a secure bonding, since photobonding breakage occurs for loads significantly higher (more than a factor 5 in the experiments carried out) than the cilliary muscle forces acting on the lens zonulae and capsular bag in human eyes.

The overlapped pHEMA/capsular bag area was 21 $mm^2$, on average.

The average bonding resistance (load per bonded area) was 1 $g/mm^2$.

At higher irradiances (0.65 $W/cm^2$) photobonding breakage was never observed for exposure times higher than 30 s. Instead, for this irradiance the rupture was produced in the capsular bag, suggesting that the photobonding may introduce structural changes in the capsular bag, making it more brittle. Capsular bag breakage occurred at much higher loads (55 g for 0.65 $W/cm^2$, 180 s exposure time) in tissue from pigmented rabbits than from New Zealand albino rabbits.

The experiment was repeated for an irradiance of 0.45 $W/cm^2$ and exposure times between 60 and 180 s in a nitrogen environment, by placing the capsular bag-polymer strip system in a chamber connected to a nitrogen pump.

Figure 7:
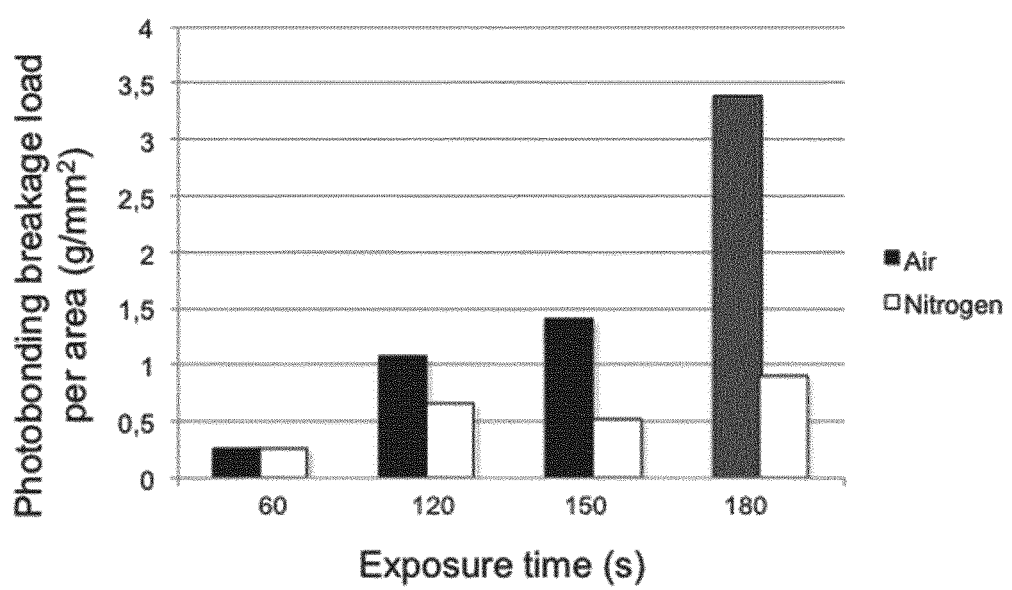
FIG. 7 is a diagram showing the loads per photobonded area that produced breakage of the capsule-pHEMA bonding in air and in a nitrogen environment.

FIG. 7 shows the loads per photobonded area that produced breakage of the capsule-pHEMA bonding in air and in a nitrogen environment, for irradiance of 0.45 $W/cm^2$ and different exposure times. For a direct comparison with the photobonding in air, the stress values are normalized by the photobonded area, which was on average 15.41±4.54 $mm^2$ in the experiments in air, and 18.86±5.26 $mm^2$ in the experiments in nitrogen. For all the exposure conditions, photobonding was significantly weaker in the nitrogen environment. For example, for a exposure time of 120 s breakage of the photobonding occurred for a stress per area 1.63 times higher in air than in hydrogen environment. Capsular breakage occurred in air for the longer exposure time. These results indicate that the presence of oxygen facilitates the photochemical processes involved in the capsular bag-polymer bonding.

In another example an intraocular lens was bonded to a capsular bag by means of photochemically-induced bonding.

This example illustrates the bonding of the haptics of a pHEMA-MMA intraocular lens to the anterior lens capsule, intraocularly, demonstrating the feasibility of the procedure intraocularly.

Enucleated rabbit eyes were obtained less than 4 hours post-mortem. The cornea was cut, and the crystalline lens material was aspirated using a Simcoe cannula through a 5-mm diameter anterior lens capsulorhexis. A 2-plate haptic pHEMA-MMA Akreos lens (by Bausch and Lomb®) was stained in a 0.1% Rose Bengal solution during 2 minutes, and then inserted in the capsular bag. An air bubble (1 ml approximately) was infused in the vitreous cavity of the eye using a 25-gauge needle. The air bubble created pressure between the capsular bag inner wall and the IOL and haptic plates. The whole eye was immersed in saline solution in a cuvette and the cuvette placed under the light delivery system. The cuvette was shifted laterally, such that the optical axis of the instrument was 2-mm-off centered from the IOL apex. The estimated peak irradiance was 0.25 W/cm$^2$ at the location of one haptic and 0.05 W/cm$^2$ at the location of the second haptic. Exposure time was 300 s.

After exposure the IOL was cut in two pieces inside the capsular bag. Strong bonding was achieved between the anterior capsular bag the haptic of the lens that had been exposed to the higher irradiance, while no bonding was achieved between for the haptic of the lens that had been exposed to the lower irradiance.

In an additional procedure in a different eye, the IOL implantation was done under similar conditions, but in this case the capsular bag was stained with a solution of 0.1% Rose Bengal using 30 gauge cannula during the hydro-dissection maneuver (injection of rose Bengal in the plane between the capsular bag and the lens cortex) after performing the anterior capsulorhexis. The IOL was then implanted through the capsulorhexis into the capsular bag. As in the former procedure, after exposure the IOL was cut in two pieces inside the capsular bag. Strong bonding was achieved between the anterior capsular bag and the haptic of the lens that had been exposed to the higher irradiance, while no bonding was achieved between for the haptic of the lens that had been exposed to the lower irradiance.

In another setting the cornea and the iris were removed, and a scleral window was performed to expose the lens equator. Then the capsular bag was emptied through a 6-mm diameter capsulorhexis and the capsule was stained with Rose Bengal during the hydro-dissection maneuver. Then a piece of pHEMA re-hydrated in Rose Bengal was introduced through the rhexis and placed against the equator with a forceps. In that position irradiation was performed through the scleral window (0.65 mW/cm$^2$, 150 s). Then a silicone tube was glued to the pHEMA piece with cyanoacrylate. To evaluate the strength of the photobonding the sclera and the silicone tube were clamped to the two arms of the stretcher. Strong photobonding was obtained, with capsular breakage occurring while capsular bag-pHEMA was still bonded. The estimated bonding resistance was 0.85 g/mm$^2$.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure.

The invention claimed is:

1. A method for implanting an intraocular lens (IOL) inside a capsular bag of an eye, the method including the steps of:
    i) providing an intraocular lens comprising:
        a central optical portion;
        at least two polymer haptics radially extending from said central optical portion for fixation of the intraocular lens inside a capsular bag of an eye, wherein each of the at least two haptics comprises: (i) a curved plate defining a capsular-contacting surface, and (ii) a photoinitiating agent delivery means contained in at least one portion of haptic and configured for providing a photoinitiating agent activatable by light for creating a photochemical bond between the intraocular lens and the capsular bag; and
        means for making the intraocular lens to be in a stretched state in order to maximize contact between the at least two haptics and the capsular bag,
    ii) providing a light source for providing light of a wavelength adapted to excite the photoinitiating agent for creating a photochemical bond between the intraocular lens and the capsular bag,
    iii) impregnating an outer surface of the curved plates of the at least two haptics with said photoinitiating agent,
    iv) introducing the intraocular lens inside the capsular bag of the eye, and
    v) irradiating said outer surface of the curved plates of the at least two haptics with light when there is contact between the outer surface of the curved plates of the at least two haptics and an inner surface of the capsular bag, such that the intraocular lens is photochemically bonded to the capsular bag of the eye,
        wherein the photoinitiating agent delivery means comprises multiple microfluidic channels extending longitudinally through the at least two haptics and through which the photoinitiating agent can flow for delivering the photoinitiating agent towards said outer surface of the curved plates of the at least two haptics,
        wherein the photoinitiating agent is a solution containing riboflavin or Rose Bengal and the light source provides light having UV, blue or green wavelength,
        wherein the at least two haptics are made of a polyhydroxyethylmethacrylate (pHEMA)-based polymer material.

2. The method for implanting an intraocular lens of claim 1, wherein the means for making the intraocular lens to be in a stretched state comprises at least one tension ring or at least one balloon.

3. The method for implanting an intraocular lens of claim 2, further comprising a plurality of light guiding elements.

4. The method for implanting an intraocular lens of claim 3, wherein the plurality of light guiding elements are embedded in the at least one tension ring or the at least one balloon.

5. The method for implanting an intraocular lens of claim 1, wherein the means for making the intraocular lens to be in a stretched state are part of the intraocular lens and are removable.

6. The method for implanting an intraocular lens of claim 1, wherein light is irradiated for a duration less than 600 seconds.

7. The method for implanting an intraocular lens of claim 1, wherein the step of irradiating with light is carried out at an irradiance below 0.65 W/cm$^2$.

* * * * *